United States Patent
Gebrian et al.

(10) Patent No.: US 7,169,356 B2
(45) Date of Patent: *Jan. 30, 2007

(54) RANDOM ACCESS REAGENT DELIVERY SYSTEM FOR USE IN AN AUTOMATIC CLINICAL ANALYZER

(75) Inventors: Peter Louis Gebrian, Wilmington, DE (US); Timothy Patrick Evers, Wilmington, DE (US)

(73) Assignee: Dade Behring Inc., Deerfield, IL (US)

( * ) Notice: Subject to any disclaimer, the term of this patent is extended or adjusted under 35 U.S.C. 154(b) by 183 days.

This patent is subject to a terminal disclaimer.

(21) Appl. No.: 10/623,310

(22) Filed: Jul. 18, 2003

(65) Prior Publication Data

US 2005/0013735 A1   Jan. 20, 2005

(51) Int. Cl.
*G01N 35/00* (2006.01)
(52) U.S. Cl. .......................................... 422/64; 422/63
(58) Field of Classification Search ................. 422/63, 422/64, 65, 66, 67; 436/44, 47, 48
See application file for complete search history.

(56) References Cited

U.S. PATENT DOCUMENTS

| | | | |
|---|---|---|---|
| 5,814,277 A | 9/1998 | Bell et al. | |
| 5,849,247 A | 12/1998 | Uzan et al. | |
| 5,856,194 A | 1/1999 | Arnquist et al. | |
| 5,885,529 A | 3/1999 | Babson et al. | |
| 5,902,549 A | 5/1999 | Mimura et al. | |
| 6,027,691 A | 2/2000 | Watts et al. | |
| 6,103,193 A | 8/2000 | Iwahashi et al. | |
| 6,193,933 B1 | 2/2001 | Sasaki et al. | |
| 6,261,521 B1 | 7/2001 | Mimura et al. | |
| 6,571,934 B1 * | 6/2003 | Thompson et al. | 198/619 |
| 6,605,213 B1 | 8/2003 | Ammann et al. | |
| 6,723,288 B2 * | 4/2004 | Devlin et al. | 422/65 |
| 6,808,304 B2 * | 10/2004 | Gebrian et al. | 366/110 |

* cited by examiner

*Primary Examiner*—Jill Warden
(74) *Attorney, Agent, or Firm*—Leland K. Jordan (57) ABSTRACT

A random access reagent container handling system using a reagent container shuttle to move reagent containers between a loading tray and at least one linear reagent container tray and at least one circular reagent carousel. The reagent container tray is positioned as needed beneath the reagent container shuttle by a reagent tray shuttle.

7 Claims, 9 Drawing Sheets

RANDOM ACCESS REAGENT DELIVERY SYSTEM FOR USE IN AN AUTOMATIC CLINICAL ANALYZER

FIELD OF THE INVENTION

The present invention relates to an apparatus for automatically processing a patient's biological fluids such as urine, blood serum, plasma, cerebrospinal fluid and the like. In particular, the present invention provides an automated system for receiving and delivering reagent containers to a reagent handling location and/or to a reagent container transfer shuttle.

BACKGROUND OF THE INVENTION

Various types of tests related to patient diagnosis and therapy can be performed by analysis assays of a sample of a patient's infections, bodily fluids or abscesses. Such patient samples are typically placed in sample vials, extracted from the vials, combined with various reagents in special reaction cuvettes or tubes, frequently incubated, and analyzed to aid in treatment of the patient. In typical clinical chemical analyses, one or two assay reagents are added at separate times to a liquid sample, the sample-reagent combination is mixed and incubated within a reaction cuvettes. Analytical measurements using a beam of interrogating radiation interacting with the sample-reagent combination, for example turbidimetric or fluorometric or absorption readings or the like, are made to ascertain end-point or rate values from which an amount of analyte may be determined using well-known calibration techniques.

Although various known clinical analyzers for chemical, immunochemical and biological testing of samples are available, analytical clinical technology is challenged by increasing needs for improved levels of analysis. Due to increasing pressures on clinical laboratories to reduce cost-per-reportable result, there continues to be a need for improvements in the overall cost performance of automated clinical analyzers. In particular, sample analysis continuously needs to be more effective in terms of increasing assay throughput or reducing the cost thereof.

A positive contributor to increasing assay throughput is the ability to provide a continuous supply of the reagents required to perform a wide range of clinical assays, including immunoassays.

U.S. Pat. No. 6,261,521 discloses a sample analysis system having a plurality of analysis units placed along a main conveyor line prior to operation. The system setup of analysis units in combination with different types of reagent supply units, and setup of analysis items for each analysis unit as to which analysis item should be assigned to which analysis unit having which reagent supply type.

U.S. Pat. No. 6,103,193 discloses an automatic immunoassay apparatus which has means for dispensing a labeled reagent into a reaction tube as well as means for dispensing an assaying reagent into the reaction tube U.S. Pat. No. 6,027,691 discloses an automatic chemistry analyzer in which a reagent probe arm assembly includes a reagent probe arm, a hollow reagent probe and a rotatable reagent stirring rod. The reagent probe is disposed generally vertically in the reagent probe arm and is movable by a reagent probe motor between a lower reagent probe position and an upper reagent probe position.

U.S. Pat. No. 5,902,549 discloses a multi-analyzer system in which analyzer units have sampling lines used as transferring routes to/from a transfer line, means for measuring reaction processes defined by specified sample and reagent in a reaction vessel and plural reagent delivery mechanisms, some are based on a pipette method, and the others based on a dispenser method.

U.S. Pat. No. 5,885,529 discloses an immunoassay analyzer having a rotatable reagent carousel which accommodates a plurality of wedge-shaped reagent packs each capable of holding a plurality of different reagents in separate compartments formed in each pack.

U.S. Pat. No. 5,849,247 discloses an immunoassay analyzer having two turntables supporting assay reagents.

U.S. Pat. No. 5,814,277 discloses an immunoassay analyzer having a turntable which removably supports a plurality of sample containers and a plurality of larger reagent containers in a circular array.

SUMMARY OF THE INVENTION

The principal object of the invention is to provide a highly flexible, random access reagent container handling system based upon reagent container shuttles adapted to remove reagent containers from a loading tray and to dispose reagent container into any of at least one reagent server. In addition, the shuttle removes reagent containers from the servers and disposes them into concentric reagent carousels and is also adapted to move reagent containers between the two concentric reagent carousels, or between servers as required. Any one of the reagent containers disposed in reagent container trays may be located at a loading position beneath the reagent container shuttle or at a reagent aspiration location by additional reagent container shuttles. This system thus provides a random access reagent supply system with the flexibility to position a large number of different reagent containers at different aspiration locations by moving reagent containers between a reagent container loading tray, at least one reagent server, and at least one reagent carousel.

BRIEF DESCRIPTION OF THE DRAWINGS

The invention will be more fully understood from the following detailed description thereof taken in connection with the accompanying drawings which form a part of this application and in which.

DETAILED DESCRIPTION OF THE INVENTION

Figure 1:
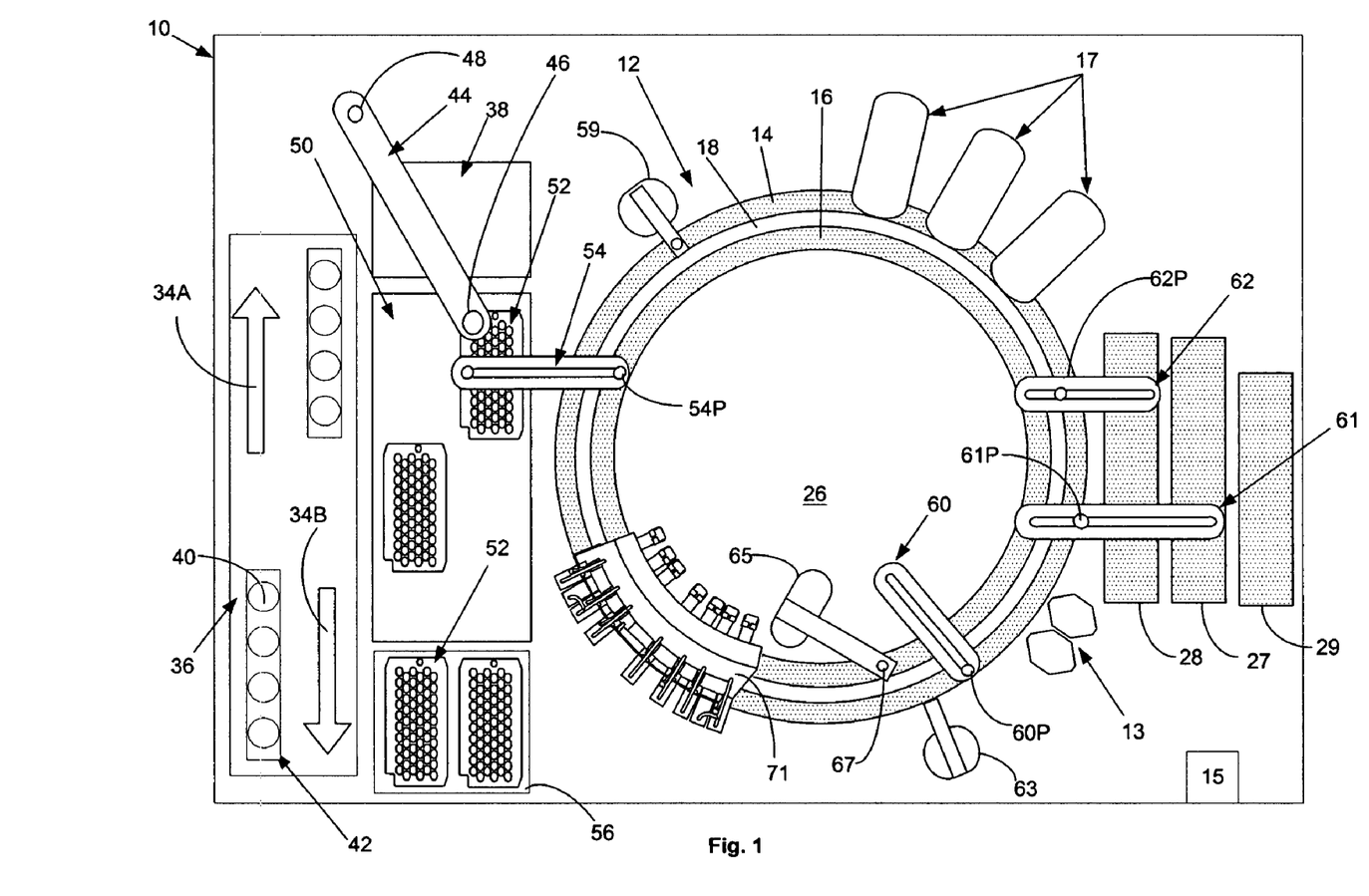
FIG. 1 is a schematic plan view of an automated analyzer in which the present invention may be employed to advantage.
Figure 2:
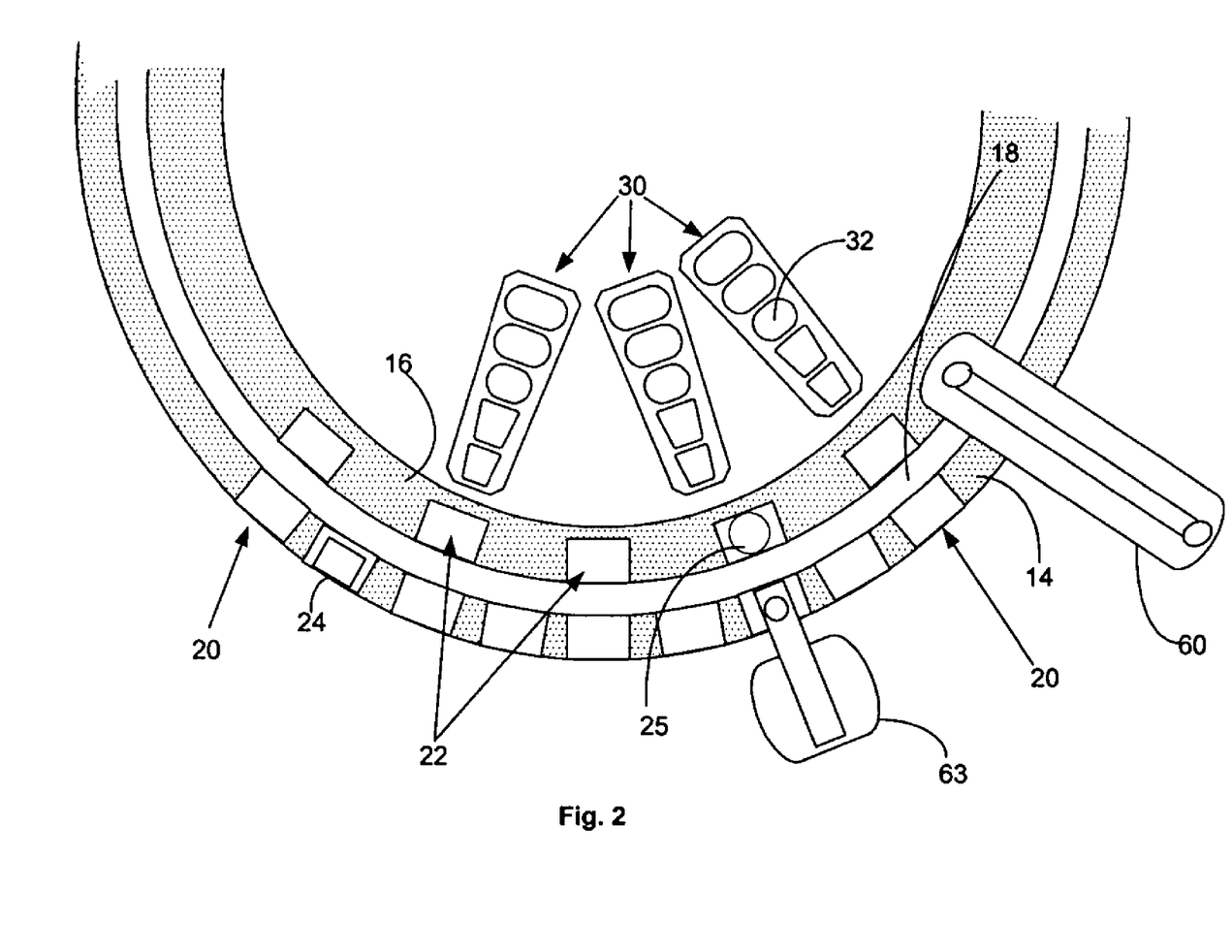
FIG. 2 is an enlarged schematic plan view of a portion of the analyzer of FIG. 1.

FIG. 1, taken with FIG. 2, shows schematically the elements of an automatic chemical analyzer 10 in which the present invention may be advantageously practiced, analyzer 10 comprising a reaction carousel 12 supporting an outer cuvette carousel 14 having cuvette ports 20 formed therein and an inner cuvette carousel 16 having vessel ports 22 formed therein, the outer cuvette carousel 14 and inner cuvette carousel 16 being separated by a open groove 18. Cuvette ports 20 are adapted to receive a plurality of reaction cuvettes 24 that contain various reagents and sample liquids for conventional clinical and immunoassay assays while vessel ports 22 are adapted to receive a plurality of reaction vessels 25 that contain specialized reagents for ultra-high sensitivity luminescent immunoassays. Reaction carousel 12 is rotatable using stepwise movements in a constant direction, the stepwise movements being separated by a constant dwell time during which carousel 12 is maintained stationary and computer controlled assay operational devices 13, such as sensors, reagent add stations, mixing stations and the like, operate as needed on an assay mixture contained within a cuvette 24.

Analyzer 10 is controlled by software executed by the computer 15 based on computer programs written in a machine language like that used on the Dimension® clinical chemistry analyzer sold by Dade Behring Inc, of Deerfield, Ill., and widely used by those skilled in the art of computer-based electromechanical control programming. Computer 15 also executes application software programs for performing assays conducted by various analyzing means 17 within analyzer 10.

Figure 5:
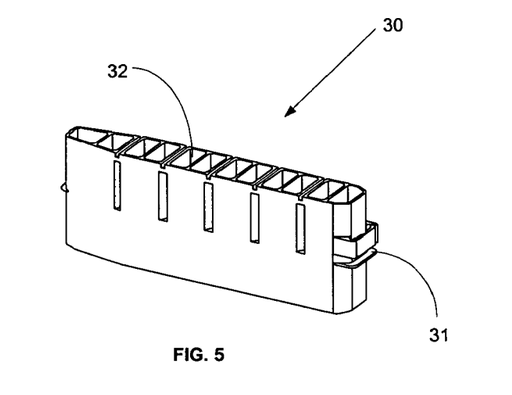
FIG. 5 is a perspective view of a reaction container useful in the analyzer of FIG. 1.
Figure 5A:
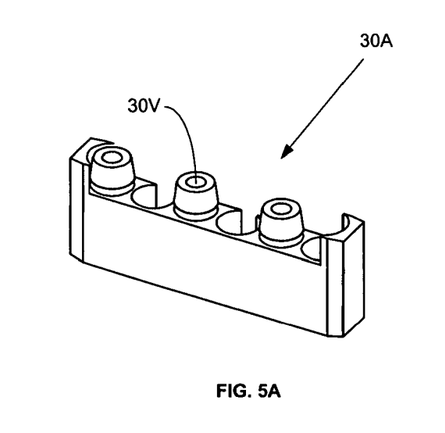

Temperature-controlled reagent storage areas 26, 27 and 28 store a plurality of multi-compartment elongate reagent cartridges 30 like that illustrated in FIG. 5 and described in co-pending application Ser. No. 09/949,132 assigned to the assignee of the present invention, or vial carriers 30A seen in FIG. 5A, and containing reagents in wells 32 as necessary to perform a given assay. A lock-out device 31 is provided to prevent accidental re-use of a previously used reagent container 30. As described later, reagent storage area 26 comprises a first reagent operation carousel 26 A, from which reagent cartridges 30 may be moved for reagent preparation operations like hydration and remix, and a second reagent operation carousel 26B, in which reagent cartridges 30 are inventoried for access by a reagent aspiration and dispense arms 60. FIG. 1 shows a preferred embodiment in which first reagent operation carousel 26A and second reagent operation carousel 26B are circular and concentric, the first reagent operation carousel 26A being inwards of the second reagent operation carousel 26B. Reagent containers 30 or reagent vial containers 30A may be loaded by an operator by placing such containers 30 or 30A into a container loading tray 29 adapted to automatically translate containers 30 or 30A to a shuttling position described later. Reagent vial containers 30A contain solutions of known analyte concentrations in vials 30V and are used in calibration and quality control procedures by analyzer 10.

A bi-directional incoming and outgoing sample tube transport system 36 having input lane 34A and output lane 34B transports incoming individual sample tubes 40 containing liquid specimens to be tested and mounted in sample tube racks 42 into the sampling arc of a liquid sampling arm 44. Liquid specimens contained in sample tubes 40 are identified by reading bar coded indicia placed thereon using a conventional bar code reader to determine, among other items, a patient's identity, the tests to be performed, if a sample aliquot is to be retained within analyzer 10 and if so, for what period of time. It is also common practice to place bar coded indicia on sample tube racks 42 and employ a large number of bar code readers installed throughout analyzer 10 to ascertain, control and track the location of sample tubes 40 and sample tube racks 42.

Figure 3:
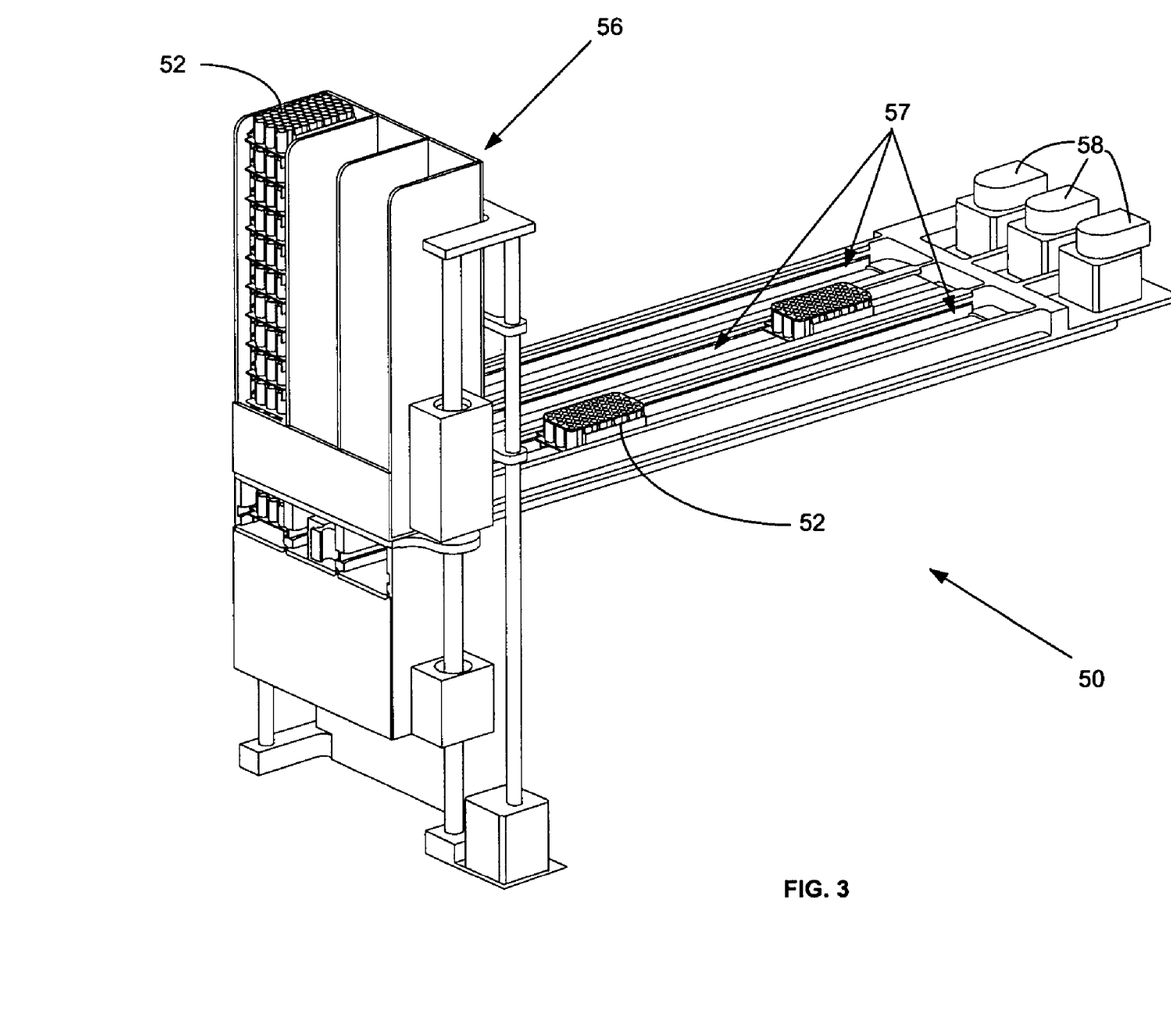
FIG. 3 is a perspective elevation view of an automated aliquot vessel array storage and handling unit of the analyzer of FIG. 1.
Figure 4:
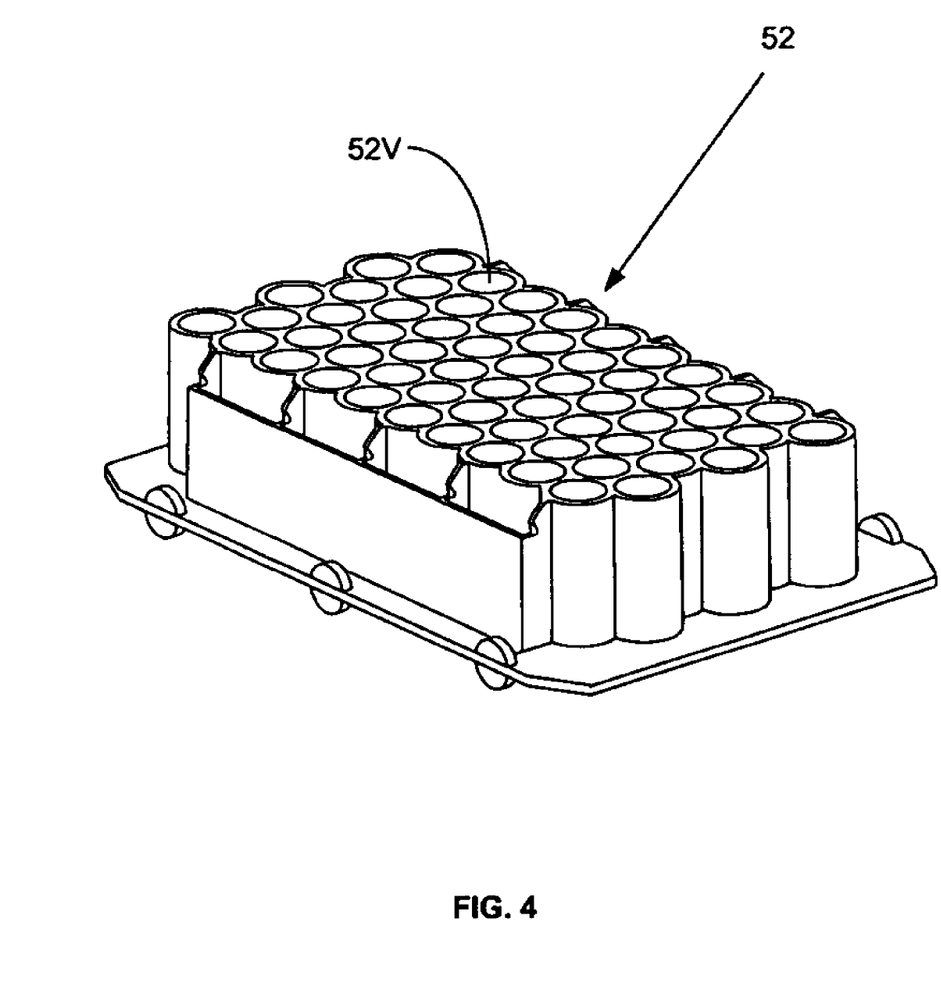
FIG. 4 is perspective elevation view of an aliquot vessel array useful in the analyzer of FIG. 1.

Sampling arm 44 supports a liquid sampling probe 46 mounted to a rotatable shaft 48 so that movement of sampling arm 44 describes an arc intersecting the sample tube transport system 36 and an aliquot vessel array transport system 50, as seen in FIG. 3. Sampling arm 44 is operable to aspirate liquid sample from sample tubes 40 and to dispense an aliquot sample into one or more of a plurality of vessels 52V in aliquot vessel array 52, as seen in FIG. 4, depending on the quantity of sample required to perform the requisite assays and to provide for a sample aliquot to be retained by analyzer 10 within environmental chamber 38.

Aliquot vessel array transport system 50 comprises an aliquot vessel array storage and dispense module 56 and a number of linear drive motors 58 adapted to bi-directionally translate aliquot vessel arrays 52 within a number of aliquot vessel array tracks 57 below a sample aspiration and dispense arm 54 located proximate reaction carousel 12. Sample aspiration and dispense arm 54 is controlled by computer 15 and is adapted to aspirate a controlled amount of sample from individual vessels 52V positioned at a sampling location within a track 57 using a conventional liquid probe 54P and then liquid probe 54P is shuttled to a dispensing location where an appropriate amount of aspirated sample is dispensed into one or more cuvettes 24 in cuvette ports 20 for testing by analyzer 10 for one or more analytes. After sample has been dispensed into reaction cuvettes 24, conventional transfer means move aliquot vessel arrays 52 as required between aliquot vessel array transport system 50, environmental chamber 38 and a disposal area, not shown.

A number of reagent aspiration and dispense arms 60, 61 and 62 comprising conventional liquid reagent probes, 60P, 61P and 62P, respectively, are independently mounted and translatable between reagent storage areas 26, 27 and 28, respectively and outer cuvette carousel 14. Probes 60P and 62P comprise conventional mechanisms for aspirating reagents required to conduct specified assays at a reagenting location from wells 32 in an appropriate reagent cartridge 30, the probes 60P, 61P and 62P subsequently being shuttled to a reagent dispensing location where reagent(s) are dispensed into reaction cuvettes 24 contained in cuvette ports 20 in outer cuvette carousel 14. Additional probes may be provided to provide increased flexibility if desired. A number of reagent cartridges 30 are inventoried in controlled environmental conditions inside reagent storage areas 26, 27 and 28; a key factor in maintaining high assay throughput of analyzer 10 is the capability to inventory a large variety of reagent cartridges 30 inside reagent storage areas 26A and 26B, 27 and 28 and to then quickly transfer random ones of these reagent cartridges 30 to reagenting locations for access by probes 60P, 61P and 62P.

Reaction cuvette load station 63 and reaction vessel load station 65 are respectively positioned proximate outer cuvette carousel 14 and inner vessel carousel 16 and are adapted to load reaction cuvettes 24 into cuvette ports 20 sideways as described later and reaction vessels 25 into vessel ports 22 using for example a translatable robotic arm 67.In operation, used cuvettes 24 in which an assay has been finally conducted, are washed and dried in a wash station 71 like disclosed in published U. S. Patent Application No. 2005/0014274 assigned to the assignee of the present invention. Subsequent assays are conducted in cleaned used cuvettes 24 unless dictated otherwise for reasons like disclosed in co-pending application Ser. No. 10/318,804 assigned to the assignee of the present invention. Cuvette unload station 59 is adapted to remove unusable reaction cuvettes 24 from cuvette ports 20 again using a translatable robotic arm 67 like seen on load stations 63 and 65.

Figure 6:
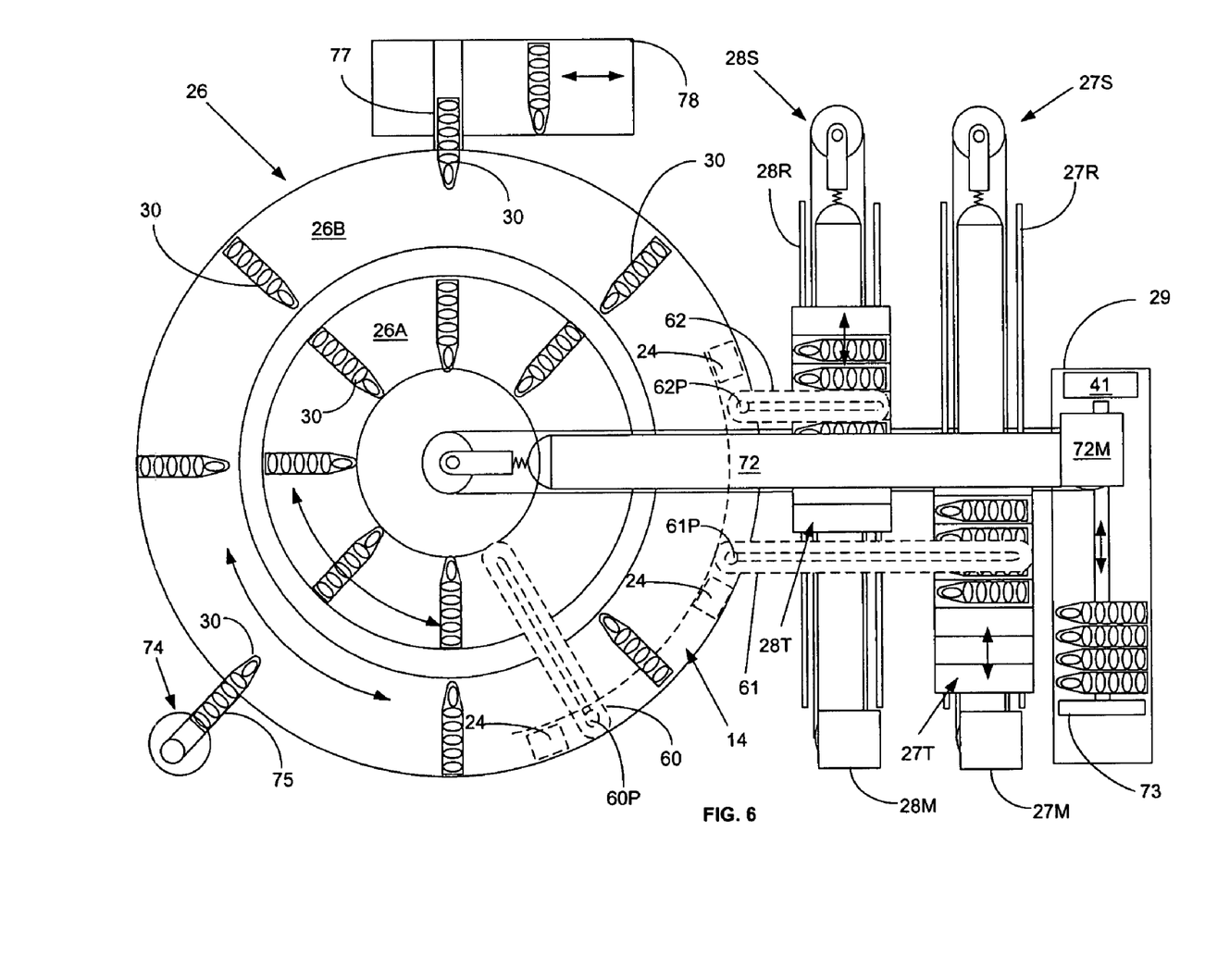
FIG. 6 is a top plan view of a random-access reagent container management system illustrative of the present invention.
Figure 7:
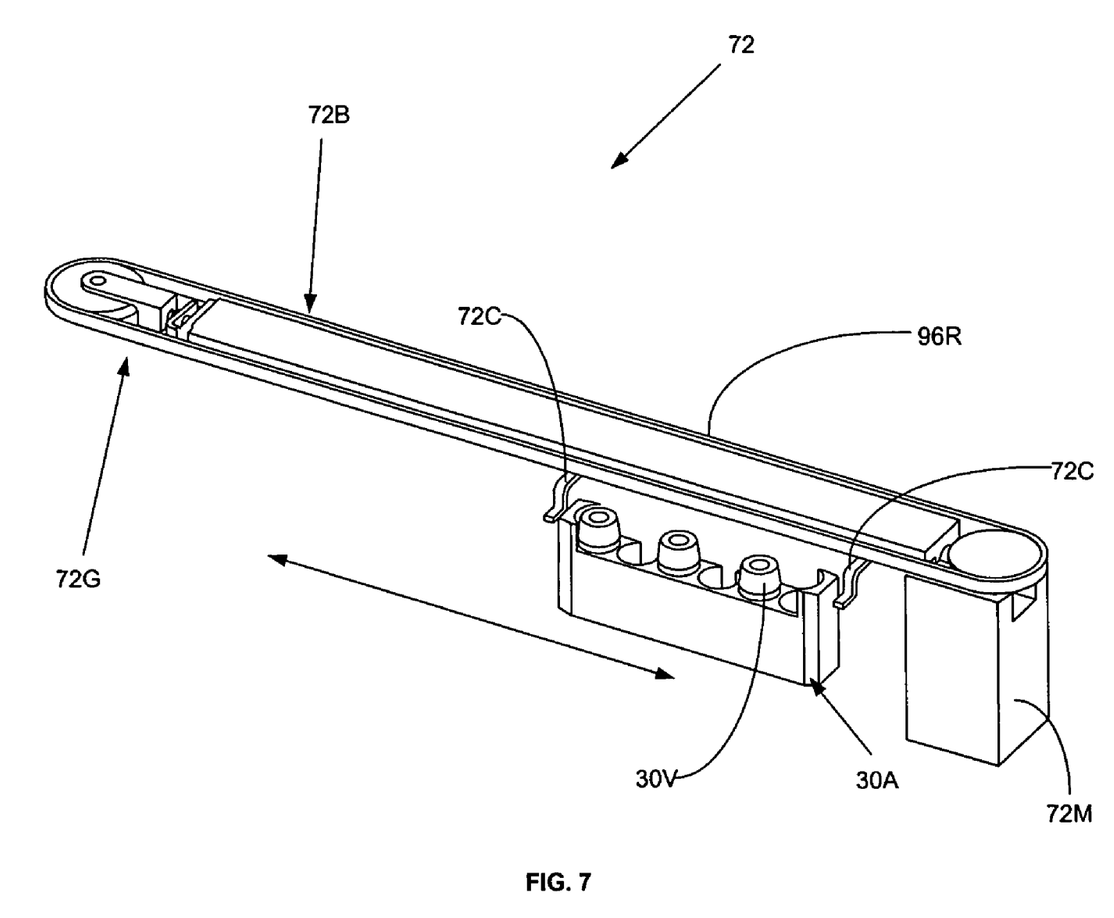
FIG. 7 is a perspective view of a first container shuttle useful in the analyzer of FIG. 1.

FIG. 6 illustrates the present invention as comprising a single, bi-directional linear reagent container shuttle 72 adapted to remove reagent containers 30 from reagent container loading tray 29 having a motorized rake 73 that automatically locates containers 30 at a loading position beneath reagent container shuttle 72. Reagent containers 30 are identified by the type of assay chemicals contained in wells 32 using conventional barcode-like indicia and a bar-code-reader 41 proximate reagent container loading tray 29. Computer 15 is programmed to track the location of each and every reagent container 30 as it is transported within analyzer 10. Shuttle 72 is further adapted to dispose a reagent container 30 into slots in at least one slotted reagent container tray 27T or 28T within at least one reagent storage area 27 or 28, respectively. For the purpose of illustration, two slotted reagent container trays 27T and 28T are shown and the invention will be described in an embodiment employing both. It should be understood that the selection of two slotted reagent container trays 27T and 28T is not a limiting feature of the present invention as it is only required that one such slotted reagent container tray 27T or 28T be employed. In a similar fashion, shuttle 72 is even further adapted to remove reagent containers 30 from reagent container trays 27T and 28T and to dispose such reagent containers 30 into either of two concentric reagent carousels 26A and 26B within reagent storage area 26. Shuttle 72 is also adapted to move reagent containers 30 between the two concentric reagent carousels 26A and 26B. As indicated by the double-headed arc-shaped arrows, reagent carousel 26A may be rotated in both directions so as to place any particular one of the reagent containers 30 disposed thereon beneath reagent aspiration arm 60. Although reagent carousel 26B may also contain reagent containers 30 accessible by reagent aspiration arm 60, in a preferred embodiment, carousel 26B is designated only for storing excess inventory of reagent containers 30 and vial containers 30A having calibration or quality control solutions therein. Any one of the reagent containers 30 disposed in reagent container trays 27T and 28T may be located at a loading position beneath reagent container shuttle 72 or at a reagent aspiration location beneath aspiration and dispensing arms 61 and 62, respectively, by reagent container shuttles 27S and 28S within reagent storage areas 27 and 28, respectively. Hereinafter, the term "server" is meant to define the combination of either reagent container shuttle 27S or 28S and either reagent storage area 27 or 28 and either reagent container tray 27T or 28T, respectively. Reagent container shuttles 27S and 28S are similar in design to reagent container shuttle 72 as seen in FIG. 7. Reagent aspiration arms 60, 61 and 62 are shown in dashed lines to indicate that they are positioned above the surfaces of reagent containers 30 inventoried in carousel 26B, and reagent container trays 27T and 28T, respectively. Reaction cuvettes 24 supported in outer cuvette carousel 14 are also both shown in dashed lines to indicate that they are positioned above the surfaces of reagent containers 30.

From this description, it is clear to one skilled in the art that the capabilities of shuttle 72 to move reagent containers 30 between reagent container loading tray 29, reagent container trays 27T and 28T, and reagent carousels 26A and 26B, taken in combination with the capabilities of shuttles 27S and 28S to move reagent containers 30 in reagent container trays 27T and 28T to appropriate aspiration locations (or to a loading location beneath shuttle 72) and with the capability of reagent carousels 26A and 26B to place any reagent container 30 beneath reagent aspiration arm 60, provide a random access reagent supply system with the flexibility to position a large number of different reagent containers at different aspiration locations. The speed at which shuttles 72, 27S and 28S transport reagent containers 30 within analyzer 10 may be a time limiting factor within the system as described; as discussed later, these shuttles 72, 27S and 28S are equipped with automatic tension controls that significantly increase shuttle speed so that the time required for reagent supply in analyzer 10 is not a throughput limitation.

FIG. 6 also shows a reagent preparation station 74 connected to reagent operation carousel 26B by means of a first reagent container transfer device 75. Reagent preparation station 74 is adapted to perform a number of reagent preparation operations like chemical additions, re-mixing, hydrating dry reagent powders and the like as may be required. In addition, a motorized belt shuttle 78 connected to reagent operation carousel 26B by means of a second reagent container transfer device 77, thereby enabling an exchange of reagent containers 30 between similarly equipped analyzers.

Bi-directional motorized belt shuttle 78 is provided so that reagent containers may be moved out of analyzer 10 and transferred to another analyzer 10 when at least two automatic clinical analyzers 10 are linked together in a dual operation like disclosed in U. S. Pat. No. 6,723,288 assigned to the assignee of the present invention. The bi-directional belt shuttle 78 is adapted to move only a single reagent or vial container or sample rack or aliquot vessel array at a time between the two or more analyzers 10.The analyzers 10 are essentially machine-wise identical to one another except that the menu of assays capable of being performed on the individual analyzers 10 may be optionally and selectively different; i.e., both analyzers 10 are equipped with physically identical sample handling, reagent storage and sample processing and assaying devices, etc. However, both analyzers 10 may be equipped with a slightly different inventory of reagents stored on-board in different kinds of reagent containers 30 so that the analyzers 10 are initially capable of performing a slightly different menu of assays. In a stand-alone mode, each analyzer 10 has an independently operable bi-directional incoming and outgoing automated sample rack transport system 36, so that samples 40 to be tested may be placed onto an analyzer 10, automatically subjected to the requested assay protocols, and returned to an inventory of samples 40 finally tested. However, when the analyzers 10 are linked together by bi-directional shuttle 78, the bi-directional incoming and outgoing sample rack transport system 36 of a first one of the two analyzers 10 is automatically converted into a one-way incoming sample rack transport system 36 adapted to receive all sample racks 42 carrying sample tubes 40 to be analyzed by either analyzer 10. In a similar manner, the incoming sample tube transport system 36 of a second of the two analyzers 10 is automatically converted into a one-way outgoing transport system 36 adapted to dispose of all sample racks 42 having sample tubes 40 with samples finally tested by either analyzer 10. Because the bi-directional shuttle 78 is adapted to move only a single sample rack 42 or reagent container 30 between analyzers 10, in the event that one of the two analyzers 10 experiences an operating failure or in the event that the bi-directional shuttle 78 experiences an operating failure, the analyzer system may automatically revert to a single analyzer system employing only the operational analyzer 10 and samples 40 may be supplied only to and analyzed only by the operational analyzer 10.

Reagent container shuttles 72, 27S and 28S are adapted to automatically compensate for unknown changes in length of a drivebelt by maintaining a constant tension on a drivebelt regardless of rapid changes in its driving direction so that reagent containers 30 may be accurately positioned at their intended location beneath reagent container shuttle 72 or within as the drivebelt wears as disclosed in published U. S. Patent Application No. 2005/0014588 assigned to the assignee of the present invention.

Figure 8:
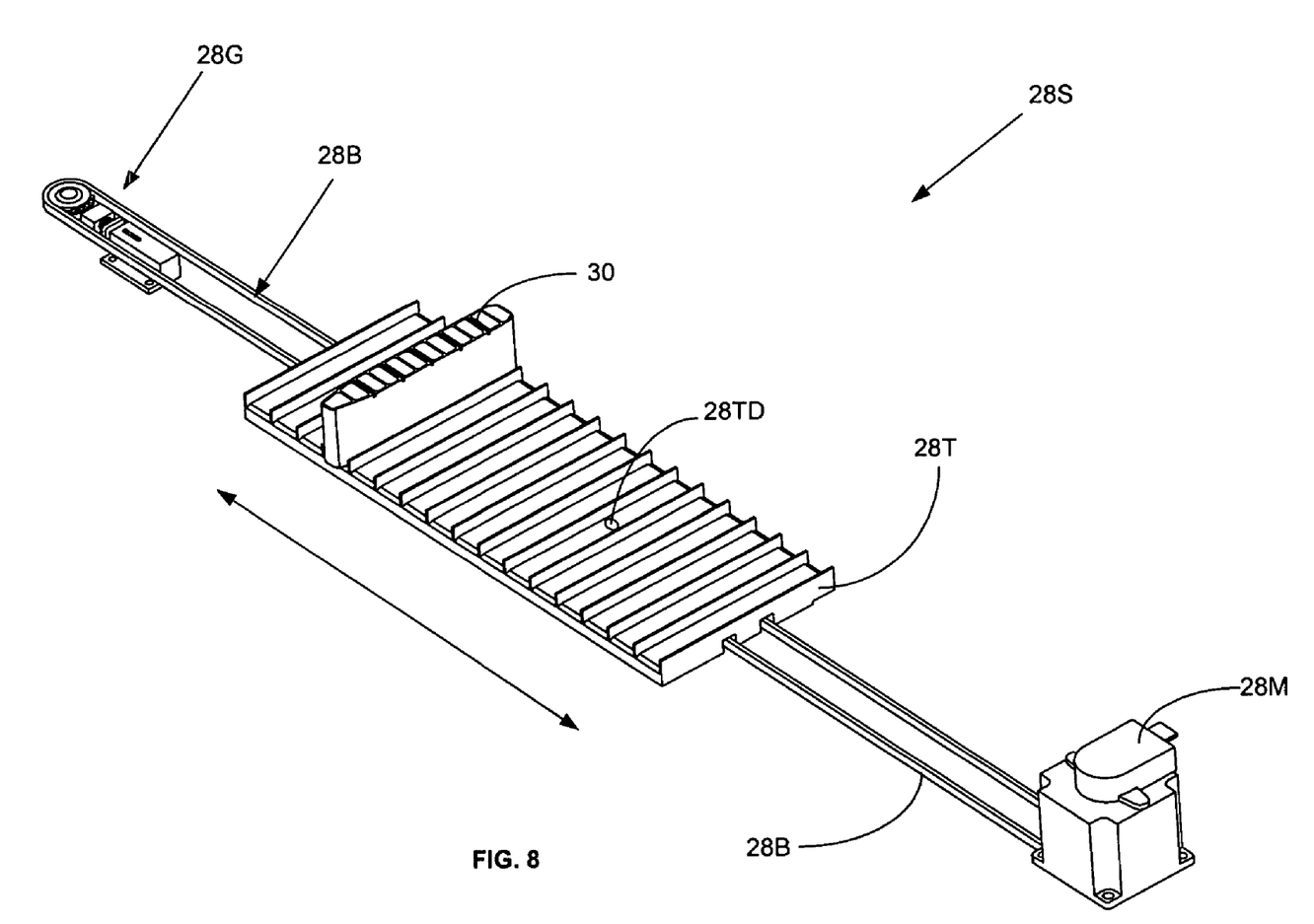
FIG. 8 is a perspective view of a second container shuttle useful in the analyzer of FIG. 1.

In the instance that reagent container shuttle 72 is transferring either a single reagent container 30 or a reagent vial container 30A as seen in FIG. 7, shuttle 72 comprises an automated tensioner 72G to compensate for changes in length a shuttling drivebelt 72B may experience during use or for changes in tension the drivebelt 72B may experience during abrupt reversals of direction so that reagent cartridges 30 may be precisely positioned at their intended location as the drivebelt 72B wears. In an exemplary use of tensioner 72G, a motor 72M is controlled by computer 15 to circulate drivebelt 72B in clockwise and counter-clockwise directions in order to position reagent vial containers 30A or reagent cartridges 30 within slots in reagent operation carousels 26S and 26A. In FIG. 7, drivebelt 72B has vial container 30A attached thereto by means of edge guides 72C so that vial container 30A containing vials 30V of calibration or control liquids, for example, is shuttled bi-directionally along the direction indicated by the double-headed arrow. Similarly and as seen in FIG. 8, reagent container tray 28T is shown secured by a tie-down 28TD only on one leg of drivebelt 28B so that tray 28T is free to be driven to and from along the direction of drivebelt 28B, as indicated by the double-ended arrow. Consequently, reagent cartridges 30 within slots in tray 28T may be automatically positioned at a pick-up location beneath reagent container shuttle 72.

In operation of analyzer 10 using the random access reagent delivery system described above, consider a very simplified instance in which seven particular reagent containers 30 and one reagent container 30A are loaded by an operator into container loading tray 29. For purposes of illustration only, consider that:

1. the first reagent container 30, designated RC1, requires hydration of dry reagent contained therein prior to aspiration and use in sample analysis;
2. the second reagent container 30, designated RC2, contains reagents therein suitable for immediate aspiration and use in a sample analysis having a high demand frequency;
3. the third reagent container 30, designated RC3, contains reagents therein suitable for immediate aspiration and use in a sample analysis having a low demand frequency;
4. the fourth reagent container 30, designated RC4, contains reagents therein suitable for immediate aspiration and use in a sample analysis to be performed upon an analyzer other than analyzer 10;
5. the fifth reagent container 30, designated RC5, contains reagents therein suitable for immediate aspiration and use in a sample analysis different from the sample analysis reagents in the second reagent container RC2 but also having a high demand frequency;
6. the sixth reagent container 30, designated RC6, contains reagents therein suitable for immediate aspiration and use in a sample analysis different from the sample analysis reagents in the third reagent container RC3 but also having a low demand frequency; and,
7. the seventh reagent container 30, designated RC7, contains reagents therein suitable for immediate aspiration and use in a calibration protocol to be performed on analyzer 10.

Figure 9:
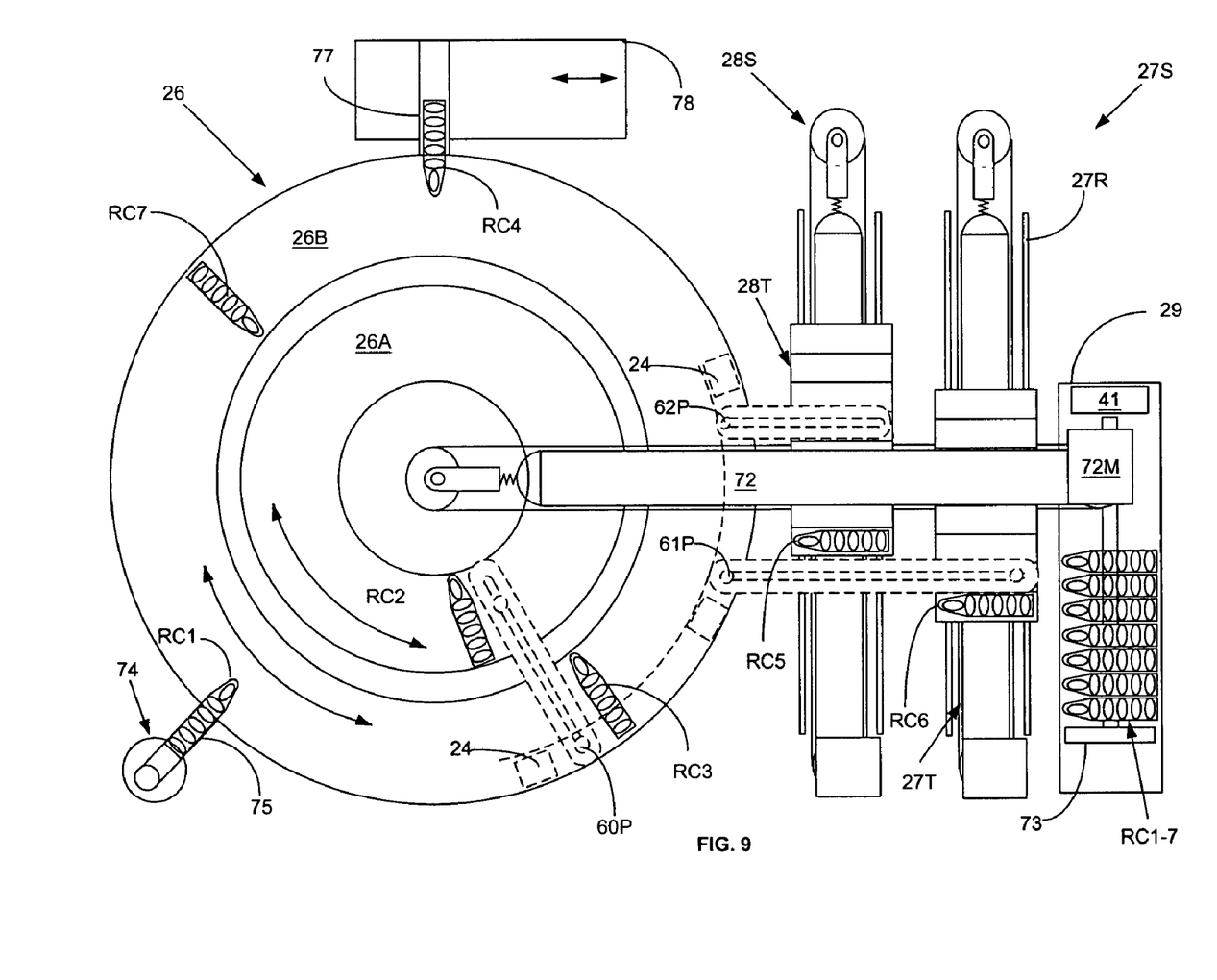
FIG. 9 is a simplified top plan view of a random-access reagent container management system of FIG. 6.

A simplified FIG. 9 illustrates such an instance in that initially all seven RC1–RC7 reagent containers are placed into container loading tray 29. Each separate reagent container RC1–RC7 is identified by barcode reader 41 and the system of shuttles 70, 27S, and 28S and reagent carousels 26A and 26B are controlled by computer 15 to position the reagent containers RC1–RC7 at their appropriate locations as described in the following Table 1, taken in conjunction with FIGS. 6 and 9. Before any reagent container RC1–RC7 is further moved onto analyzer 10, the condition of lock-out device 31 is checked to ensure against accidental re-use of a previously used reagent container 30.

TABLE 1

| Reagent Container | Operation of Analyzer 10 |
|---|---|
| RC1 | Rake 73 automatically locates reagent container RC1 at a loading position beneath reagent container shuttle 72, edge guides 72C confine reagent container RC1 so that shuttle 72 may be controlled to transport and position reagent container RC1 into a slot in reagent carousel 26B. Carousel 26B is rotated to position reagent container RC1 at first cartridge transfer device 75 which transfers reagent container RC1 into reagent preparation station 74 wherein the appropriate reagent preparation is conducted. Subsequent to an operation like hydration, reagent container RC1 is transferred back onto into a slot in reagent carousel 26B for temporary storage until such time the reagents in reagent container RC1 are needed to accomplish an assay scheduled on analyzer 10; carousel 26B is then transferred by shuttle 72 from reagent carousel 26B into an empty slot in reagent carousel 26A and reagents aspirated therefrom by probe 60P on arm 60. Arm 60 is then operated to position probe 60P over the appropriate reaction cuvette 24 in outer cuvette carousel 14 so that the requisite reagents from reagent container RC1 may be dispensed thereinto. |
| RC2 | In a manner similar to RC1, rake 73 automatically locates reagent container RC2 at a loading position beneath reagent container shuttle 72, edge guides 72C confine reagent container RC2 so that shuttle 72 may be controlled to transport and position reagent container RC2 into a slot in reagent carousel 26B. Whenever reagents from RC2 are needed to perform an assay on analyzer 10, reagent container RC2 is transferred by shuttle 72 from reagent carousel 26B into an empty slot in reagent carousel 26A and reagents aspirated therefrom by probe 60P on arm 60. Arm 60 is then operated to position probe 60P over the appropriate reaction cuvette 24 in outer cuvette carousel 14 so that the requisite reagents from reagent container RC2 may be dispensed thereinto. |
| RC3 | In a manner similar to RC2, rake 73 automatically locates reagent container RC3 at a loading position beneath reagent container shuttle 72, edge guides 72C confine reagent container RC3 so that shuttle 72 may be controlled to transport and position reagent container RC3 into a slot in reagent carousel 26B. Whenever reagents from RC3 are needed to perform an assay on analyzer 10, reagent container RC3 is transferred by shuttle 72 from reagent carousel 26B into an empty slot in reagent carousel 26A and reagents aspirated therefrom by probe 60P on arm 60. Arm 60 is then operated to position probe 60P over the appropriate reaction cuvette 24 in outer cuvette carousel 14 so that the requisite reagents from reagent container RC3 may be dispensed thereinto. |

TABLE 1-continued

| Reagent Container | Operation of Analyzer 10 |
|---|---|
| RC4 | In a manner similar to RC1, rake 73 automatically locates reagent container RC4 at a loading position beneath reagent container shuttle 72, edge guides 72C confine reagent container RC4 so that shuttle 72 may be controlled to transport and position reagent container RC4 into a slot in reagent carousel 26A. Carousel 26A is rotated to position reagent container RC4 at second cartridge transfer device 77 which transfers reagent container RC7 onto motorized belt shuttle 76 which is operated to transfer reagent container RC4 to an analyzer other than analyzer 10. |
| RC5 | In a manner similar to RC1, rake 73 automatically locates reagent container RC5 at a loading position beneath reagent container shuttle 72, edge guides 72C confine reagent container RC5 so that shuttle 72 may be controlled to transport and position reagent container RC5 into a slot in reagent container tray 28T. Whenever reagents from RC5 are needed to perform an assay on analyzer 10, shuttle 28S is operated to position RC5 beneath arm 62 which is operated to position probe 62P over the appropriate well 32 in reagent container RC5 so that the requisite reagents may be aspirated. Arm 62 is then operated to position probe 62P over the appropriate reaction cuvette 24 in outer cuvette carousel 14 so that the requisite reagents from reagent container RC5 may be dispensed thereinto. |
| RC6 | In a manner similar to RC5, rake 73 automatically locates reagent container RC6 at a loading position beneath reagent container shuttle 72, edge guides 72C confine reagent container RC6 so that shuttle 72 may be controlled to transport and position reagent container RC6 into a slot in reagent container trays 27T. Whenever reagents from RC6 are needed to perform an assay on analyzer 10, shuttle 273 is operated to position RC6 beneath arm 61 which is operated to position probe 61P over the appropriate well 32 in reagent container RC6 so that the requisite reagents may be aspirated. Arm 61 is then operated to position probe 61P over the appropriate reaction cuvette 24 in outer cuvette carousel 14 so that the requisite reagents from reagent container RC6 may be dispensed thereinto. |
| RC7 | In a manner similar to RC3, rake 73 automatically locates reagent vial container RC7 at a loading position beneath reagent container shuttle 72, edge clamps 72C clamp reagent container RC7 so that shuttle 72 may be controlled to transport and position reagent container RC7 into a slot in reagent carousel 26B where it remains until needed in conducting a calibration protocol on analyzer 10. At that time, reagent carousel 26B is rotated to position RC7 beneath arm 60 which is operated to position probe 60P over the appropriate vial 30V in reagent container RC7 so that the requisite calibration solutions may be aspirated. Arm 60 is then operated to position probe 60P over the appropriate reaction cuvette 24 in outer cuvette carousel 14 so that the requisite calibration solutions from reagent container RC7 may be dispensed thereinto. |

It is to be understood that the embodiments of the invention disclosed herein are illustrative of the principles of the invention and that other modifications may be employed which are still within the scope of the invention. For instance, whenever a number of assays have been performed by analyzer 10 so that any reagent container 30 is expiring of a reagent, an alert message may be provided so that an operator may place a new reagent container 30 into container loading tray 29 and the operation in Table 1 carried out to replace the expiring reagent container. Similarly, if a reagent container contains time-sensitive reagents and a critical number of days have passed since the reagent container 30 was initially put into use on analyzer 10, an alert message may be provided so that an operator may place a new reagent container 30 into container loading tray 29 and the operation in Table 1 carried out to replace the out-dated reagent container. These and other similar operational uses may be made employing the system of shuttles 70, 27S, and 28S and reagent carousels 26A and 26B to position reagent containers 30 at desirable locations throughout analyzer 10 so as to maximize assay throughput. For these reasons, the present invention is not limited to those embodiments precisely shown and described in the specification but only by the following claims.

We claim:

1. A random access reagent container or vial container supply system comprising:
   a reagent container or a vial container loading tray (29);
   at least one carousel (26A);
   at least one storage tray (27) positioned between the loading tray (29) and the carousel (26A); and,
   a bi-directional linear shuttle (72) having means for removing reagent containers (30) or vial containers (30A) from the loading tray, and having means for placing reagent containers or vial containers into the carousel.

2. The reagent supply system of claim 1 wherein the loading tray includes a motorized rake adapted to automatically position the containers beneath the linear shuttle.

3. The reagent supply system of claim 1 having first and second concentric reagent carousels, the first carousel being inwards of the second carousel, the linear shuttle adapted to move reagent containers between the first and second concentric reagent carousels.

4. The reagent supply system of claim 3 further including a first reagent container transfer device proximate the second concentric reagent carousel to transfer reagent containers from the second concentric reagent carousel to a reagent preparation station.

5. The reagent supply system of claim 3 further including a second reagent container transfer device proximate the second concentric reagent carousel to transfer reagent containers from the second concentric reagent carousel to a motorized belt shuttle.

6. The random access reagent container or vial container supply system of claim 1 wherein said shuttle further comprises means for removing reagent containers from the loading tray and placing containers into the storage tray.

7. An automatic chemical analyzer comprising the reagent supply system of claim 1 and further comprising a reaction carousel having cuvette ports formed therein to receive a plurality of reaction cuvettes, and reagent aspiration and dispense arms to aspirate reagents from reagent containers in the reagent carousel and in the reagent server and to dispense reagents into the reaction cuvettes.

* * * * *